(12) United States Patent
Thomas et al.

(10) Patent No.: US 8,709,718 B1
(45) Date of Patent: Apr. 29, 2014

(54) METHOD OF TREATING LUNG CANCER

(75) Inventors: Roman K. Thomas, Cologne (DE); Martin L. Sos, Cologne (DE); Jonathan Weiss, Melbourne (DE)

(73) Assignee: Max-Planck-Gesellschaft zur Forderung der Wissenschaften E.V., Munich (DE)

( * ) Notice: Subject to any disclaimer, the term of this patent is extended or adjusted under 35 U.S.C. 154(b) by 0 days.

(21) Appl. No.: 13/371,399

(22) Filed: Feb. 11, 2012

Related U.S. Application Data

(60) Provisional application No. 61/442,184, filed on Feb. 12, 2011.

(51) Int. Cl.
*C12Q 1/68* (2006.01)
*C12P 19/34* (2006.01)

(52) U.S. Cl.
USPC .......................................... 435/6.1; 435/91.2

(58) Field of Classification Search
None
See application file for complete search history.

(56) References Cited

FOREIGN PATENT DOCUMENTS

WO WO2006089087 A2 8/2006

OTHER PUBLICATIONS

Pardo O.E. et al. Cancer Res 2009; 69: (22). Nov. 15, 2009, pp. 8645-8651.*
Bass et al., "SOX2 Is an Amplified Lineage Survival Oncogene in Lung and Esophageal Squamous Cell Carcinomas" Nat Genet. Author manuscript; available in PMC May 1, 2010.
Dutt et al., "Inhibitor-Sensitive FGFR1 Amplification in Human Non-Small Cell Lung Cancer" PLoS One 6(6): e20351 (Jun. 2011).
Flemming, "Hope for smoking-associated lung cancer?" Nature Review Drug Discovery. vol. 10: 98 (Feb. 2011).
Tonon et al., "High-resolution genomic profiles of human lung cancer" PNAS 102 (27): 9625-9630 (Jul. 5, 2005).
Turner et al., "A Therapeutic Target for Smoking-Associated Lung Cancer" Sci. Transl. Med. 2 (62), 62ps56 (Dec. 15, 2010).
Weiss et al., "Frequent and Focal FGFR1 Amplification Associates with Therapeutically Tractable FGFR1 Dependency in Squamous Cell Lung Cancer" Sci. Transl. Med. 2 (62), 62ra93 (Dec. 15, 2010).
Zhao et al., "Homozygous Deletions and Chromosome Amplifications in Human Lung Carcinomas Revealed by Single Nucleotide Polymorphism Array Analysis" Cancer Res 2005; 65 (13): 5561-5570 (Jul. 1, 2005).

* cited by examiner

*Primary Examiner* — Stephen Kapushoc
(74) *Attorney, Agent, or Firm* — Jun He Law Offices P.C.; James J. Zhu

(57) ABSTRACT

A method of predicting a lung cancer patient's response to FGFR inhibitors is disclosed herein, particularly in patients with squamous cell lung cancer.

13 Claims, 12 Drawing Sheets

METHOD OF TREATING LUNG CANCER

CROSS-REFERENCE TO RELATED US APPLICATIONS

This application claims the benefit of U.S. Provisional Application No. 61/442,184 filed on Feb. 12, 2011, the content of which are incorporated by reference herein in its entirety.

FIELD OF THE INVENTION

The present invention generally relates to therapeutic methods, and particularly to a biomarker-based method of treating non-small cell lung cancer using an FGFR inhibitor.

BACKGROUND OF THE INVENTION

Oncogenic protein kinases are frequently potential targets for cancer treatment. Examples include ERBB2 amplification in breast cancer, associated with clinical response to antibodies targeting ERBB2 (see Slamon, et al., *N. Engl. J. Med.*, 344, 783-792 (2001)), and KIT or PDGFRA mutations in gastrointestinal stromal tumors, which lead to sensitivity to the KIT/ABL/PDGFR inhibitor imatinib (see Heinrich et al., *J. Clin. Oncol.*, 21, 4342-4349 (2003)). In lung adenocarcinoma, patients with EGFR-mutant tumors experience tumor shrinkage and prolongation in progression-free survival when treated with EGFR inhibitors. See Pao et al., *Proc Natl Acad Sci USA* 101, 13306-13311 (2004); Paez et aL, *Science* 304, 1497-1500 (2004); Lynch et al., *N. Engl. J. Med.*, 350, 2129-2139 (2004); Mok, et al., *N. Engl. J. Med.* 361, 947-957 (2009). Furthermore, EML4-ALK gene fusion-positive lung cancers can be effectively treated with ALK inhibitors. Soda et al., *Nature* 448, 561-566 (2007); Kwak et al., *N Engl J Med* 363, 1693-1703). However, these alterations almost exclusively occur in the rare adenocarcinomas of patients who never smoked, but are uncommon in squamous-cell lung cancer, which is almost invariably associated with smoking. Khuder, *Lung Cancer* 31, 139-148 (2001).

Although previous studies have reported recurrent genetic alterations in squamous-cell lung cancer (see e.g., Bass, *Nat Genet.* 41, 1238-1242 (2009), no therapeutically tractable targets have so far been identified. Thus, therapeutic options for squamous-cell lung cancer patients remain scarce, as molecularly targeted drugs such as erlotinib, gefitinib, pemetrexed and cetuximab are either poorly active (see Mok, et al., *N. Engl. J. Med.* 361, 947-957 (2009); Pirker et al., *Lancet* 373, 1525-1531 (2009)) or contraindicated (e.g. bevacizumab)(see Sandler et al., *N Engl J Med* 355, 2542-2550 (2006)). These observations emphasize the need for new "druggable" targets in squamous-cell lung cancer patients.

SUMMARY OF THE INVENTION

The inventors have surprisingly discovered that focal FGFR1 gene amplification is a recurrent event in squamous-cell lung cancer, but rarely in other lung cancer subtypes, and that the apoptosis-inducing effect of FGFR inhibitors is dependent upon FGFR1 amplification. Specifically, FGFR inhibitors inhibited growth and induced apoptosis specifically in those lung cancer cells carrying amplified FGFR1, but not in lung cancer cells in which the FGFR1 gene is not amplified. The identification of focal and recurrent amplification of FGFR1 in squamous-cell lung cancer represents the first therapeutically amenable target in this histological type of lung cancer that is strongly associated with smoking and resistance to heretofore known targeted lung cancer drugs.

Accordingly, the present invention provides a method of predicting a patient's response to an FGFR1 inhibitor. The method includes the steps of selecting a patient having squamous cell lung cancer, determining in squamous cell lung cancer cells obtained from the patient, the presence or absence of focal FGFR1 gene amplification, wherein the presence of focal FGFR1 gene amplification would indicate that the patient has an increased likelihood of response to an FGFR inhibitor, and wherein absence of said focal FGFR1 gene amplification would indicate that the patient is less likely to respond to an FGFR inhibitor.

In another aspect, the present invention provides a method of treating squamous cell lung cancer, comprising the steps of identifying a patient having squamous cell lung cancer, determining in squamous cell lung cancer cells obtained from the patient, the presence or absence of focal FGFR1 gene amplification, and administering to the patient an effective amount of an FGFR1 inhibitor when the focal FGFR1 gene amplification is detected, and administering to the patient a treatment regimen free of FGFR1 inhibitors when the focal FGFR1 gene amplification is absent in the squamous cell lung cancer cells.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

Figure 1:
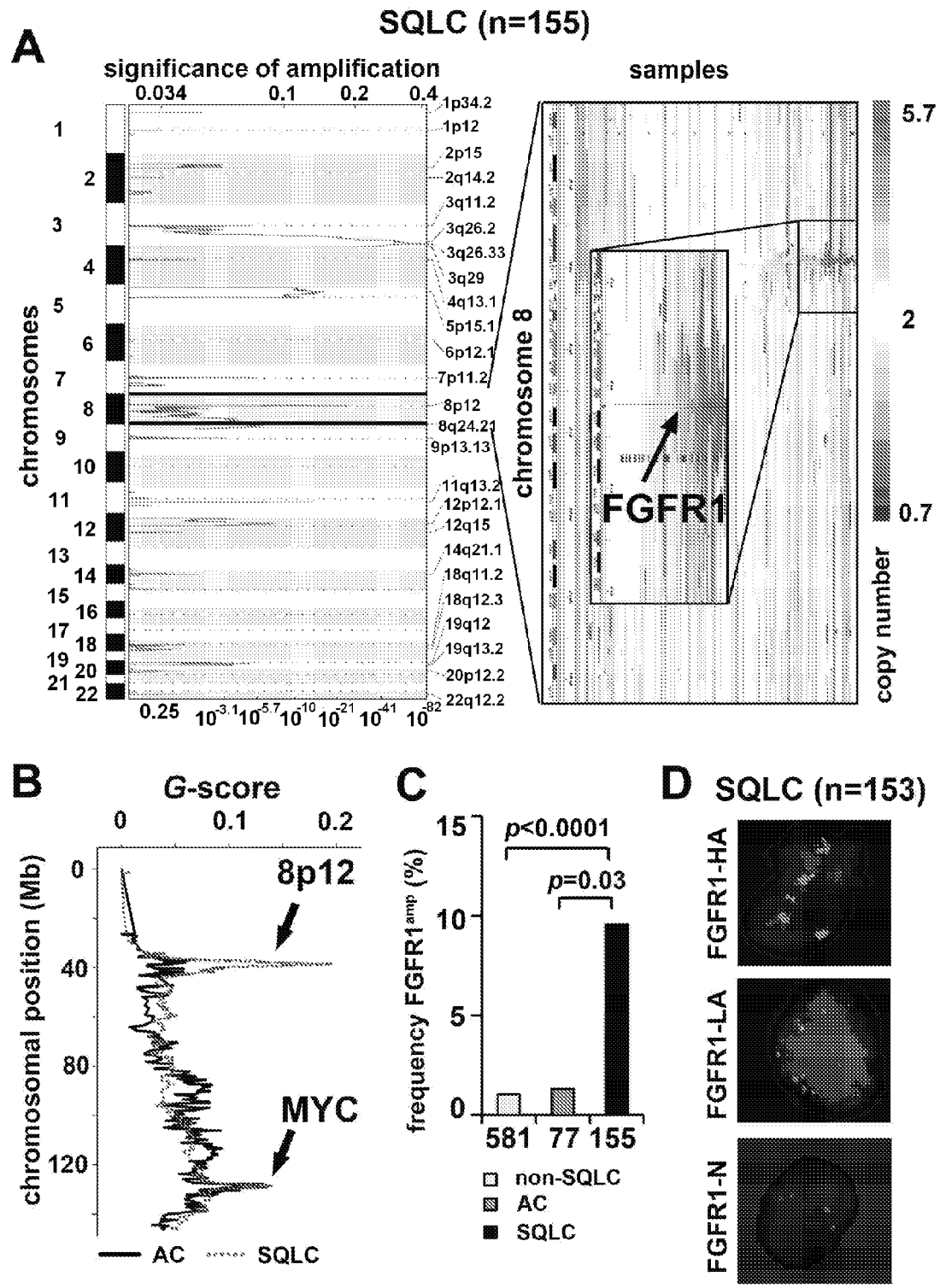
FIG. 1. FGFR1 is amplified in squamous-cell lung cancer. (A) Left panel: Significant (FDR-value; x-axis) amplifications across all chromosomes (y-axis) in squamous-cell lung cancer (SQLC; n=155) as assessed by GISTIC. Right panel: Copy-number alterations (blue=deletion; white=copy number-neutral; red=amplification) at chromosome 8 (y-axis) across all SQLC samples (x-axis). Samples are ordered according to focal amplification of FGFR1. (B) Significant (G-score; y-axis) copy number changes in adenocarcinoma (AC; n=77), (black line) and SQLC (red dotted line) at chromosome 8. The q-value for the presence of 8p12 amplification is $8.82*10^{-28}$ for squamous-cell lung cancer and greater than 0.25 for adenocarcinoma. The chromosomal positions of FGFR1 (8p12) and MYC are highlighted (black arrows) (C) Frequency of FGFR1 amplification (% of samples≥copy number 4; y-axis) in non-SQLC lung cancer from a published dataset, AC and SQLC. P-values indicate statistical significance. (D) FISH analysis (green=control; red=FGFR1) of 153 SQLC samples (FGFR1-HA: copy number>9; FGFR1-LA: copy number>2<9; FGFR1-N: copy number 2). Presented are example images from the three different FGFR1 amplification groups.

Thus far, there has been no suitable "druggable" target identified in squamous cell lung cancer, and effective targeted therapy for this lung cancer subtype has not been available.

The inventors have now surprisingly discovered that focal FGFR1 amplification is frequent in squamous-cell lung cancer (9.7% of 155 cases), but not in other non-small cell lung cancer subtypes. The inventors further surprisingly discovered, in both cell lines and in vivo, that FGFR inhibitors inhibit growth and induce apoptosis specifically in those lung cancer cells carrying amplified FGFR1. It is this specific dependency on FGFR1 amplification and the high frequency of the amplification in squamous cell lung cancer that make it desirable and also feasible for a new biomarker-based, targeted and effective therapy specifically for squamous cell lung cancer using FGFR inhibitors.

Accordingly, the present invention provides a method of predicting a lung cancer patient's response to an FGFR1 inhibitor. The method includes the steps of selecting a patient having squamous cell lung cancer, determining in squamous cell lung cancer cells obtained from the patient, the presence or absence or status of focal FGFR1 gene amplification or FGFR1 gene overexpression, wherein the presence of focal FGFR1 gene amplification or overexpression would indicate that the patient has an increased likelihood of response to an FGFR inhibitor, and wherein absence of said focal FGFR1 gene amplification or overexpression would indicate that the patient is less likely to respond to an FGFR inhibitor. In preferred embodiments, FGFR1 gene amplification status is determined.

In another aspect, the present invention provides a method of treating lung cancer, in particular squamous cell lung cancer. In the method, a patient having squamous cell lung cancer is identified. The method also includes a step of determining the presence or absence or status of focal FGFR1 gene amplification or FGFR1 gene overexpression in squamous cell lung cancer cells obtained from the patient. The determined status of focal FGFR1 gene amplification or FGFR1 gene overexpression may be used to guide the treatment decision for the patient. Specifically, a therapeutically effective amount of an FGFR1 inhibitor is administered only if focal FGFR1 gene amplification or FGFR1 gene overexpression is detected or present. Thus, the treatment method may also include a step of administering a therapeutically effective amount of an FGFR1 inhibitor in the presence of focal FGFR1 gene amplification or FGFR1 gene overexpression. When focal FGFR1 gene amplification or FGFR1 protein overexpression is absent in the squamous cell lung cancer cells, the patient is administered a treatment regimen free of FGFR1 inhibitors. In preferred embodiments, FGFR1 gene amplification status is determined.

Thus, in preferred embodiments, the method of treating lung cancer, in particular squamous cell lung cancer, comprises identifying a patient having, or diagnosing a patient as having, squamous cell lung cancer; determining the status of focal FGFR1 gene amplification or FGFR1 gene overexpression in squamous cell lung cancer cells obtained from the patient; and administering a therapeutically effective amount of an FGFR1 inhibitor to the patient.

In other preferred embodiments, the method of treating lung cancer, in particular squamous cell lung cancer, comprises identifying a patient having, or diagnosing a patient as having, squamous cell lung cancer; determining the status of focal FGFR1 gene amplification or FGFR1 gene overexpression in squamous cell lung cancer cells obtained from the patient; and administering a therapeutically effective amount of an FGFR1 inhibitor to the patient when focal FGFR1 gene amplification or FGFR1 gene overexpression is detected in the squamous cell lung cancer cells obtained from the patient. To put it differently, the method comprises administering a therapeutically effective amount of an FGFR1 inhibitor to a patient diagnosed of squamous cell lung cancer and with tumor cells determined to have focal FGFR1 gene amplification or FGFR1 gene overexpression.

In other preferred embodiments, the method of treating lung cancer, in particular squamous cell lung cancer, comprises identifying a patient having, or diagnosing a patient as having, squamous cell lung cancer; determining the status of focal FGFR1 gene amplification or FGFR1 gene overexpression in squamous cell lung cancer cells obtained from the patient; and when focal FGFR1 gene amplification or FGFR1 protein overexpression is absent in the squamous cell lung cancer cells, administering to the patient a treatment regimen free of FGFR1 inhibitors.

In the methods of the present invention, focal FGFR1 gene amplification is determined to be present when greater than 2 copies of the FGFR1 genomic DNA are detected in a cancer cell from a lung cancer patient, e.g., as measure by FISH, CISH or real-time PCR. In preferred embodiments, focal FGFR1 gene amplification is determined to be present when at least 4, 7 or 8, or more preferably at least 9 copies of the FGFR1 genomic DNA are detected in a cancer cell from a lung cancer patient, e.g., as measure by FISH, CISH or real-time PCR. The status of FGFR1 gene amplification means the presence, absence or the degree of amplification of the FGFR1 gene.

In preferred embodiments of the methods of the present invention, the step of identifying a patient having squamous cell lung cancer comprises selecting a patient with squamous cell lung cancer who is a current or past smoker, e.g., who has a smoking history of at least 1, 2 or 3 months of regularly smoking.

In some embodiments of the methods of the present invention, the presence or absence of an activating mutation in the EGFR gene is also determined in the one or more cancer cells, and wherein the presence of an EGFR-activating mutation would indicate a decreased likelihood that the patient would respond to FGFR inhibitors, and wherein the patient is administered an effective amount of an FGFR1 inhibitor when focal FGFR1 gene amplification is detected and no EGFR-activating mutation is detected, and preferably no FGFR1-resistant mutations are detected. EGFR-activating mutations refer to mutations in the EGFR kinase domains that result in activation of the kinase activity of EGFR, and such mutations are generally known in the art including, e.g., activating mutations in exons 18, 19, 20 and 21, as disclosed in the publicly accessible COSMIC database and in U.S. Pat. No. 7,964,349, the relevant content of which is incorporated herein by reference. In some embodiments, the presence or absence of activating mutations in the KRAS gene is also determined in the one or more cancer cells. Activating mutations in the KRAS gene refer to mutations in the KRAS gene that result in the activation of the kinase activity in the KRAS protein encoded by the mutant gene. Commonly occurring activating mutations in the KRAS gene are generally known in art including, e.g., the mutations in the 12th, 13th or 61th codon of the coding region of the KRAS gene, as disclosed in the publicly accessible COSMIC database.

About 70% to 80% of all lung cancer diagnosed are non-small cell lung cancer (NSCLC). NSCLC however is a group of diverse subtypes. Specifically, under the 1999 World Health Organization/International Association for the Study of Lung Cancer Histological Classification of Lung and Pleural Tumours, NSCLC is subclassified into squamous cell lung cancer, adenocarcinoma, large cell carcinoma, adenosquamous carcinoma, pleomorphic carcinoma, carcinoid tumor, salivary gland carcinoma, and unclassified carcinoma.

Squamous cell lung cancer, also known as squamous cell carcinoma of the lungs or epidermoid carcinoma, is one of the subtype of non-small cell lung cancer. Squamous cell lung cancer typically begins in squamous cells, which are thin and flat and look like fish scales. As known in the art, squamous cell lung cancer may be identified by x-ray, chest CT scan, MRI, sputum cytology, bronchoscopy, PET scan, endobronchial ultrasound, and histopathological analysis of tissue biopsies and samples. Squamous cell lung cancer is strongly associated with smoking and account for about 30% of non-small cell lung cancer. Typically, squamous cell lung cancer is centrally located arising from proximal bronchi. Pathologically, tumors form a firm gray-white mass with desmoplastic stromal reaction, and areas of necrosis and cavitation can be present. In terms of histopathology, tumor cells typically display squamous cell differentiation in the form of keratinization, pearl formation, and intercellular bridges. Detailed guideline for histological typing is provided by the WHO. See World Health Organization Histological Typing of Lung Tumours, $2^{nd}$ Edn. Geneva, World Health Organization, 1981; Travis et al., World Health Organization International Histological Classification of Tumours, Histological Typing of Lung and Pleural Tumours. 3rd Edn. Springer-Verlag, 1999.

Focal FGFR1 gene amplification or polysomy can be detected using any method known in the art. Specifically, the FGFR1 gene is located in chromosome 8 at about 8p11.2-p11.1, or about 8p11.23 to 8p11.22, such as the 133 kb region (chr8:38436349-38569287) including the FGFR1 gene as well as FLJ43582 gene. Thus, focal FGFR1 amplification or polysomy can be detected by directly measuring the copy number of the FGFR1 gene itself, or by indirectly measuring any amplification of at least part of the 133 kb region (chr8: 38436349-38569287), or amplification of the FLJ43582 gene.

A variety of techniques are known in the art suitable for detecting gene amplification or protein overexpression, or increase of genomic DNA copy numbers in a tissue or cell sample. For example, in situ hybridization using nucleic acid probes can be performed using any appropriate technique, such as fluorescence in situ hybridization (FISH) (e.g., interphase, metaphase, or fiber FISH), and chromogenic in situ hybridisation (CISH). See Pinkel et al. *Proc Natl Acad Sci USA*, 85:9138-42 (1988); Sholl et al., *Mod. Pathol.*, (10): 1028-35 (2007). Generally, labeled single-stranded nucleic acid probes can be contacted to a tissue or cell sample (e.g., fresh-frozen or FFPE tumor samples) under conditions such that the probes hybridize to the genomic region of interest in cells, and the hybrids are then detected by, e.g., fluorescence signal or enzymatic detection. For example, FGFR1CISH may be performed with FGFR1ZytoDot-SPEC Probe (Zytovision GMbH, Bremerhaven, Germany) and the SPoT-Light CISH Polymer Detection Kit (Invitrogen). See Turner et al., *Cancer Res.*, 70(5); 2085-94 (2010).

Alternatively, the multiplex ligation-dependent probe amplification (MLPA) may also be used to detect gene amplification or genomic copy number variation. See e.g., Villamon et al., *Histol. Histopathol.*, 26, 343-350 (2011); Kozlowski et al., *Electrophoresis, javascript: AL_get(this, 'jour', 'Electrophoresis.');* (23):4627-36 (2008), all of which being incorporated herein by reference.

Other suitable methods known in the art also include SNP genomic array, genomic hybridization to cDNA microarrays, comparative genomic hybridization (CGH), and spectral karyotyping (SKY). See U.S. Pat. No. 7,424,368; Heiskanen, et al., *Cancer Res.*, 60:799 (2000); Kallioniemi et al., Comparative Genomic Hybridization: A Powerful New Method for Cytogenetic Analysis of Solid Tumors, *Science*, 258:818-821 (1992); Pinkel et al., High-Resolution Analysis of DNA Copy Number Variation Using Comparative Genomic Hybridization to Microarrays, *Nat. Genet.*, 20:207-211 (1998); Schrock, et al., *Science*, 273:494-7 (1996)), all of which being incorporated herein by reference.

A preferred method for detecting gene amplification is genomic DNA-based quantitative real-time PCR or qPCR. See Königshoff et al., *Clinical Chemistry* 49: 219-229, 2003, which is incorporated herein by reference. The target DNA to be assayed may be amplified in real-time PCR by, e.g., conventional techniques such as TaqMan, Scorpion, molecular beacons, and the amount of amplified DNA product may be detected by non-sequence specific fluorescence dyes (e.g. SybrGreen), or labeled probes such as TaqMan probes, FRET probes, and molecular beacons. See Bartlett and Stirling, PCR Protocols, in *Methods in Molecular Biology*, $2^{nd}$ ed., 2003, Humana Press, Totowa, N.J., USA. For copy analysis, an exogenous DNA standard or endogenous housekeeping gene or DNA sequence can be used as a reference, as is known in the art. Quantitative real-time PCR is particularly suitable for determining FGFR1 mRNA level in a cell or tissue sample, in which case mRNA is first reverse transcribed into cDNA, which is then amplified by PCR using FGFR1-specific oligonucleotide PCR primers. This qRT-PCR method is well-known in the art.

For detecting the FGFR1 protein expression in a tumor cell or tissue sample, any known methods for measuring protein level in cells or tissue samples may be used for the present invention. Examples of such methods include, but are not limited to, immunohistochemistry (IHC), ELISA, Western blot, protein microarray, etc. Typically an antibody specifically immunoreactive with FGFR1 protein is contacted with a cell or tissue sample under conditions to allow immunoreaction with FGFR1 proteins in the sample, and the amount of bound antibody is measured. In IHC analysis, typically an FFPE tumor sample may be used. For ELISA, Western blot and protein microarray analysis, the samples may be FFPE samples or fresh frozen samples, and are preferably homogenized and extracted before contact with an FGFR1 antibody, as is generally known in the art.

In preferred embodiments, the presence or absence of focal FGFR1 gene amplification in a squamous cell lung cancer cell obtained from a patient identified as having squamous cell lung cancer, is determined by in situ hybridization (FISH) analysis, or real-time PCR.

In other preferred embodiments, the presence or absence of FGFR1 mRNA overexpression in a squamous cell lung cancer cell obtained from a patient, is determined by qRT-PCR.

In other preferred embodiments, the presence or absence of FGFR1 protein overexpression in a squamous cell lung cancer cell obtained from a patient, is determined by IHC.

FGFR1 inhibitors applicable to the methods of the presentation are generally known in the art, and are all characterized by significantly inhibiting the kinase activity of the FGFR1 protein, or specifically decreasing the amount of such kinase activity in cells. Thus, exemplary FGFR1 inhibitors include, but are not limited to, small organic molecule inhibitors of FGFR1 kinase activity, as well as siRNA and antisense molecules targeting FGFR1 mRNA, antibodies specific to FGFR1 protein and capable of antagonizing against FGF signaling through FGFR1. Various methods for identifying FGFR1 inhibitors and determining whether a compound is an FGFR1 inhibitor are generally known in the art, and are disclosed, e.g., in U.S. Pat. Nos. 5,783,683, 6,677,368, and 7,737,149, US Patent Application Publication Nos. 20040014024 and 20100273811, all of which are incorporated herein by reference. It is noted that, for purposes of the present invention, suitable FGFR1 inhibitors may or may not also act upon other targets such as VEGFRs, FGFR2, FGFR3, etc.

Examples of small molecule FGFR1 inhibitors known in the art include those disclosed in, e.g., U.S. Pat. Nos. 6,677,368, 6,855,730, 7,528,142, 7,109,219, and US Patent Application Publication Nos. 20040014024, 20050209247, 20080004302, 20080153812, 20090318468, 20100120761, 20100286209, and PCT Publication No. WO2002022598, all of which being incorporated herein by reference. Specific examples of commonly known FGFR1 inhibitors include, cediranib, brivanib (Bristol-Myers Squibb), TSU-68 (Teiho) BIBF1120 (Boehringer Ingelheim), dovitinib (Novartis), Ki23057, MK-2461, E7080 (Eisai), PD173074, SU5402, BGJ398 (Novartis), E-3810 (Ethical Oncology Science), AZD4547 (AstraZeneca), and PLX052, etc. Examples of antisense molecules targeting FGFR1 mRNA are disclosed in U.S. Pat. No. 5,783,683, which is incorporated herein by reference. Examples of FGFR1-targeting antibodies are disclosed in U.S. Pat. No. 7,498,416, which is incorporated herein by reference. A fusion protein that exhibits inhibitory effect on FGFR1 is disclosed in U.S. Pat. No. 7,678,890, which is incorporated herein by reference. In addition, sulf1-modified heparin compounds useful as FGFR1 inhibitors are also disclosed in US Patent Application Publication No. 20050227921, which is incorporated herein by reference. Methods of administering the FGFR1 inhibitors to patients for treating cancer are also disclosed in the references provided herein.

The methods of the present invention are applicable to all these FGFR1 inhibitors. Thus, methods are provided for predicting a squamous cell lung cancer patient's response to any one of such inhibitors, based on the FGFR1 gene amplifcation or gene expression status. Methods are also provided for treating a non-small cell lung cancer using one or more of the FGFR1 inhibitors, which includes selecting a patient having squamous cell lung cancer, and determining the FGFR1 gene amplifcation or gene expression status, and administering such FGFR1 inhibitors according to the status, as described in detail above.

The present invention also provides a kit for detecting FGFR1 gene amplification or overexpression in a cell or tissue sample from a obtained from a patient. The kit may include a carrier for the various components of the kit. The carrier can be a container or support, in the form of, e.g., bag, box, tube, rack, and is optionally compartmentalized. The carrier may define an enclosed confinement for safety purposes during shipment and storage. The kit also includes various components useful in detecting FGFR1 gene amplification or overexpression in accordance with the present invention using the above-discussed detection techniques. Thus, for example, the kit may include a FISH probe specific to the chromosome region spanning chr8:38436349-38569287, and the probe may be labeled with a tag. Other reagents generally required for FISH analysis may also be included. In other embodiments, the kit may include one or more oligonucleotide chips having, on a solid support, probes capable of hybridizing the FGFR1 gene sequence or part of a region spanning chr8:38436349-38569287. In another embodiment, the kit may include a pair of PCR primers useful in amplifying an FGFR1 gene sequence in real time PCR. In the above embodiments, the probe and oligonucleotides in the detection kit can be labeled with any suitable detection marker including but not limited to, radioactive isotopes, fluorephores, biotin, enzymes (e.g., alkaline phosphatase), enzyme substrates, ligands and antibodies, etc. See Jablonski et al., *Nucleic Acids Res.,* 14:6115-6128 (1986); Nguyen et al., *Biotechniques,* 13:116-123 (1992); Rigby et al., *J. Mol. Biol.,* 113:237-251 (1977). Alternatively, the probe and oligonucleotides included in the kit are not labeled, and instead, one or more markers are provided in the kit so that users may label the oligonucleotides at the time of use. In still other embodiments, the kit may include an antibody specific to FGFR1 protein and useful in immunohistochemical analysis of FGFR1 protein expression in cell or tissue sample from a patient. In addition, the detection kit preferably includes instructions on using the kit for detecting FGFR1 gene amplification or overexpression in a cell or tissue sample from a obtained from a patient, in accordance with the detailed description above.

Typically, once the FGFR1 gene amplification or overexpression status is analyzed in a lab, physicians or patients or other researchers may be informed of the result. Specifically the result may be cast in a transmittable form that can be communicated or transmitted to other researchers or physicians or genetic counselors or patients. Such a form can vary and can be tangible or intangible. The result with regard to the presence or absence of in the individual tested can be embodied in descriptive statements, diagrams, photographs, charts, images or any other visual forms. The statements and visual forms can be recorded on a tangible media such as papers, computer readable media such as floppy disks, compact disks, etc., or on an intangible media, e.g., an electronic media in the form of email or website on internet or intranet. In addition, the result may also be recorded in a sound form and transmitted through any suitable media, e.g., analog or digital cable lines, fiber optic cables, etc., via telephone, facsimile, wireless mobile phone, internet phone and the like.

The test result may be received and/or input into a computer system and processed by a computer program product in the computer system, e.g., in a hospital or clinic.

Figure 10A:
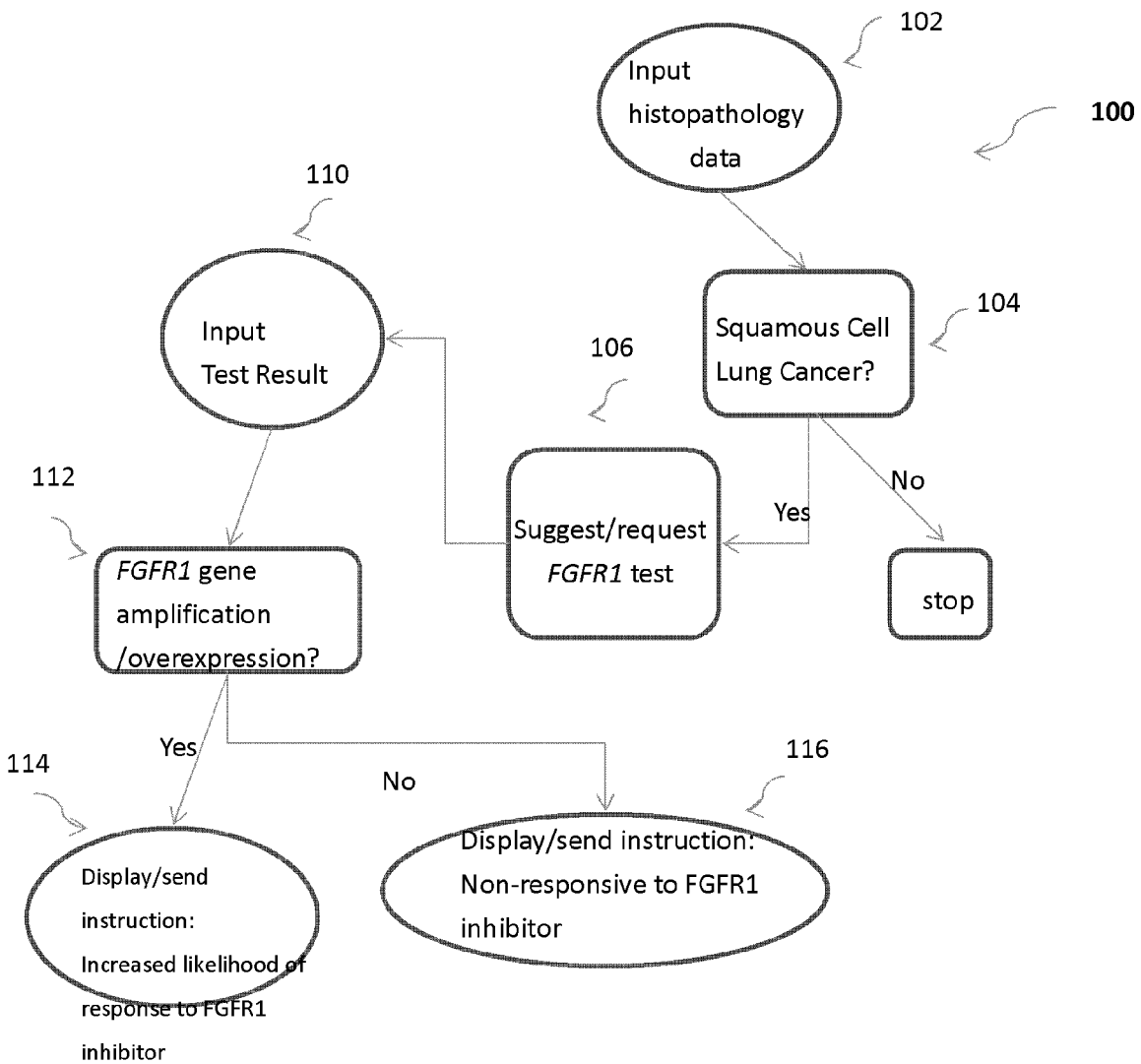
FIGS. 10A & 10B are flowcharts showing the computer program of the invention.

The present invention also provides computer program products and used in the computer system described below or other computer- or internet-based systems. Accordingly, another aspect of the present invention relates to a computer program product comprising a computer-usable medium having computer-readable program code or instructions embodied thereon for enabling a processor to carry out the process of as embodied in the flowchart in FIGS. 10A and 10B. As illustrated in the flowchart (100) in FIG. 10A, the computer program product is provided for enabling a computer system to execute a computerized process of analyzing patient test data and automatically provide an instruction or alert to a physician whether to use an FGFR1 inhibitor to treat a non-small cell lung cancer. The computer program product comprises a computer-usable medium having computer-readable program code embodied thereon for effecting a computing system to receive a first data set containing an NSCLC patient's histopathology data including the subtype characteristics of the cancer (102). The first data set can be processed or unprocessed image, an electrical signal corresponding to an unprocessed image data, or simply descriptive written statement. In step 104, the computer readable program code determines from the first data set whether the patient has squamous cell lung cancer or not. If the answer is no, then the computer program stops there, or continues to execute other functions. If the answer is yes, in step 106 the computer program product code effects the computer to display a request for FGFR1 gene amplification or overexpression status, or alternatively request and receive (step 110) from another part of the computer system information on FGFR1 gene amplification or overexpression status of the patient's tumor. In step 112, the computer program product code enables the computer to processes the information (processed or unprocessed image, an electrical signal corresponding to an unprocessed image data, or simply descriptive written statement) on the FGFR1 gene amplification or overexpression status, and determines the presence or absence of FGFR1 gene amplification or overexpression. If the answer is yes, in step 114, the computer program product code functions to enable the computer system to display, in a display module, an instruction or alert that it is suitable to use FGFR1 inhibitors to treat the patient. Alternatively, the computer program product code effects the computer system to send a data set through a communcation path to an interface module or an external device, an instruction or alert (in e.g., email, message, text message or signals) that it is suitable to use FGFR1 inhibitors to treat the patient. If the answer is no, in step 116, the computer program product code functions to enable the computer system to display, in a display module, an alert (in e.g., email, message, text message or signals) that the patient is unlikely to respond to FGFR1 inhibitors. Alternatively, the computer program product code effects the computer system to send a data set through a communcation path to an interface module or an external device, an alert (in e.g., email, message, text message or signals) that the patient is unlikely to respond to FGFR1 inhibitors.

Figure 10B:
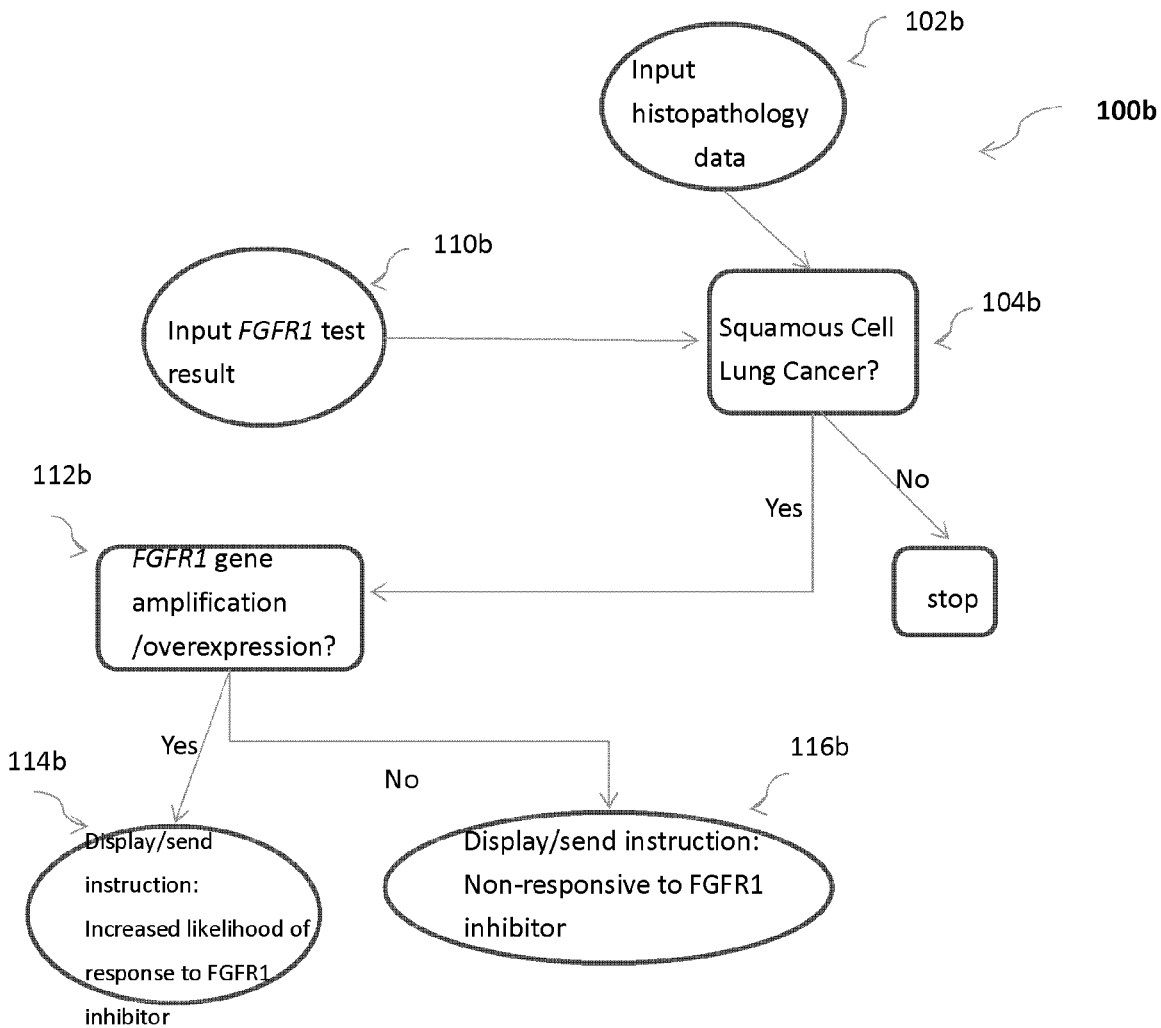

In an alternative embodiment shown in FIG. 10B, step 106 is avoided as in step 110 the test result on FGFR1 gene amplification or overexpression status is received by the computer system.

It will be understood that each block or step of the flowcharts illustration and combinations of blocks in the flowcharts can be implemented by computer program instructions. These computer program instructions may be loaded onto a computer or other programmable apparatus to produce a machine, such that the instructions which execute on the computer or other programmable apparatus create means for implementing the functions specified in the flowcharts or step(s). These computer program instructions may also be stored in a computer-readable memory or medium that can direct a computer or other programmable apparatus to function in a particular manner, such that the instructions stored in the computer-readable memory or medium produce an article of manufacture including instruction means which implement the function specified in the flowcharts or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the flowcharts or step(s).

Accordingly, the flowcharts support combinations of means for performing the specified functions, combinations of steps for performing the specified functions and program instruction means for performing the specified functions. It will also be understood that each step of the flowcharts and combinations of steps in flowcharts can be implemented by special purpose hardware-based computer systems, which perform the specified functions or steps, or combinations of special purpose hardware and computer instructions.

Figure 11:
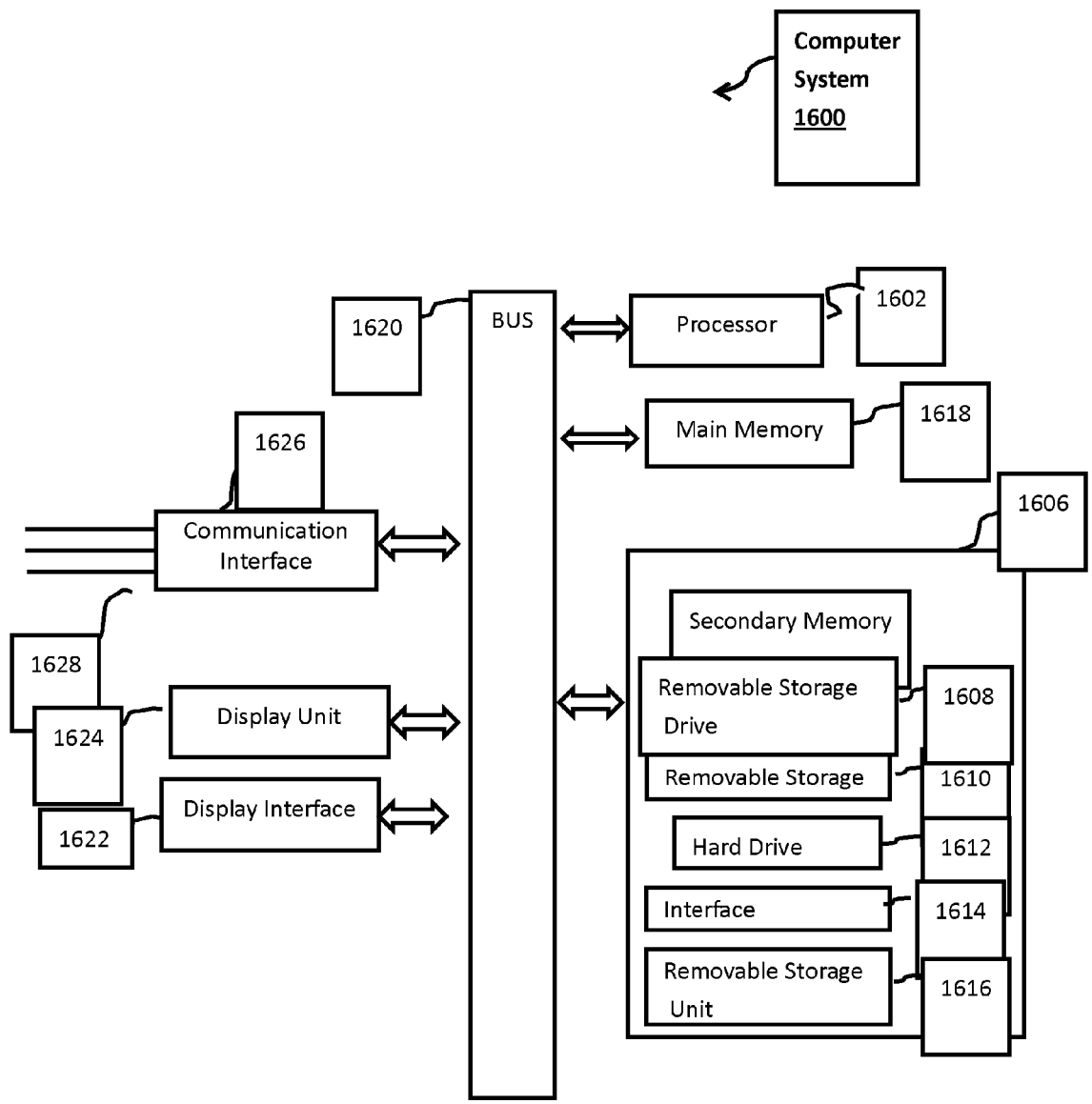
FIG. 11 is a diagram showing the computer system of the invention.

Accordingly, in accordance with yet another aspect, a computer system is provided for executing the instructions from the computer program products of the present invention. An embodiment of the system is shown in FIG. 11. Referring now to FIG. 11, system 1600 includes one or more processors, such as processor 1602. The processors can be used to execute software or computer-readable instruction codes implementing the method of the present invention described above. It must be understood that the processor may consist of any number of devices. The processor may be a data processing device, such as a microprocessor or microcontroller or a central processing unit. The processor could be another logic device such as a DMA (Direct Memory Access) processor, an integrated communication processor device, a custom VLSI (Very Large Scale Integration) device or an ASIC (Application Specific Integrated Circuit) device. In addition, the processor can be any other type of analog or digital circuitry that is designed to perform the processing functions described herein.

Computer system 1600 also includes a main memory 1618, preferably random access memory (RAM). A secondary memory 1606 may also be included. The secondary memory 1606 may include, e.g., a remove storage drive 1608, which can be in various forms, including but not limited to, a magnetic tape drive, a floppy disk drive, a VCD drive, a DVD drive, an optical disk drive, etc. The removable storage drive 1608 may be compatible with a removable storage unit 1610 such that it can read from and/or write to the removable storage unit 1610. Removable storage units typically include a computer usable storage medium having stored therein computer-readable program codes or instructions and/or computer readable data. Example of removable storage units are well known in the art, including, but not limited to, floppy disks, magnetic tapes, optical disks, and the like.

Preferably, secondary memory 1606 also includes a hard drive 1612, which can be used to store computer readable program codes or instructions, and/or computer readable data.

In addition, as shown in FIG. 11, secondary memory 1606 may further include an interface 1614 and a removable storage unit 1616 that is compatible with interface 1614 such that software, computer readable codes or instructions can be transferred from the removable storage unit 1616 into computer system 1600. Examples of interface-removable storage unit pairs include, e.g., removable memory chips (e.g., EPROMs or PROMs) and sockets associated therewith, program cartridges and cartridge interface and the like.

As shown in FIG. 11, in computer system 1600, processor 1602 as well as the main and secondary memories 1618 and 1606 are all operably linked together through communication infrastructure 1620, which may be a communications bus, system board, cross-bar, etc.). Through the communication infrastructure 1620, computer program codes or instructions or computer readable data can be transferred and exchanged.

Additionally, as discussed above especially in the context of FIG. 11, it may also be desirable to exchange data with other devices or systems located distant from the computer system 1600. For this purpose, an internet node or an intranet node including an interface module (also called communications interface) 1626 may be included in computer system 1600 such that computer-readable data (e.g., texts, tables, descriptions, photos, diagrams, etc. in the form of electronic, electromagnetic, optical or other signals), and software or other computer-readable codes or instructions may be transferred back and forth between external devices (not shown) and computer system 1600. Preferably, a communications path 1628 compatible with the communications interface 1626 is included. As will be apparent to skilled artisans, modems, communication ports, network cards such as Ethernet cards, and newly developed devices for accessing intranet or internet can all be used as the communication interface 1626.

In addition, computer system 1600 can also include a display interface 1622. Through display interface 1622, results of data analysis, e.g., in the forms of graphics, table, text, and the like from communication infrastructure 1620 may be displayed on display unit 1624.

In accordance with the present invention, the computer system implements a computer program or computer-readable codes or instructions to execute the data processing, analysis, comparison and coordination described above in various embodiments of the present invention. As such the computer readable program codes or instructions (i.e., computer instructions means for enabling processor 1602 to perform the processing, analysis, comparison and/or coordination) may be included in the computer system such as system 1600 directly or through a computer program product as described above. Examples of such computer program products in system 1600 include, e.g., removable storage units 1610 and 1616, a hard disk (not shown) in hard disk drive 1612 and a carrier wave (not shown) which delivers software or computer readable codes or instructions to system 1600 through communication interface 1626 and communication path 1628.

The computer system provided herein executes the instructions from the computer program product codes as described above.

EXAMPLES

We conducted a systematic search for alterations that are therapeutically amenable and performed high-resolution gene-copy number analyses in a set of 232 lung cancer specimens. We identified frequent (9.7% of cases) and focal FGFR1 amplification in squamous-cell lung cancer (n=155), but not in other lung cancer subtypes, and confirmed its presence in an independent cohort of squamous-cell lung cancer samples employing FISH. Using cell-based screening with the FGFR inhibitor (PD173074) in a large (n=83) panel of lung cancer cell lines, we demonstrated that this compound inhibited growth (p=0.0002) and induced apoptosis (p=0.008) specifically in those lung cancer cells carrying amplified FGFR1. We validated the dependency on FGFR1 of FGFR1-amplified cell lines by knockdown of FGFR1 and by ectopic expression of a resistance allele of FGFR1 (FGFR1$^{V561M}$), which rescued FGFR1-amplified cells from PD173074-mediated cytotoxicity. Finally we showed that inhibition of FGFR1 with a small molecule led to significant tumor shrinkage in vivo. Focal FGFR1 amplification is common in squamous-cell lung cancer and associated with tumor growth and survival, suggesting that FGFR inhibitors may be a viable therapeutic option in this cohort of patients.

Specifically, to identify therapeutically relevant genome alterations in squamous-cell lung cancer, 155 primary squamous-cell lung cancer specimens were analyzed using Affymetrix 6.0 SNP arrays, yielding high-resolution genomic profiles (median inter-marker distance<1 kb). To separate driver lesions from random noise, the GISTIC algorithm was applied. See Beroukhim et al., *Proc Natl Acad Sci USA* 104, 20007-20012 (2007); Beroukhim et al., *Nature* 463, 899-905 (2009). We identified 25 significant amplification peaks, including the previously described amplification of SOX2 on chromosome 3q26.33 (FIG. 1A) and 26 significant deletions. The second most significant amplification (q=8.24*10$^{-28}$) peak was identified on 8p12 and included FGFR1 as well as FLJ43582 in each sample called as amplified (FIG. 1A). This region spanned 133 kb (chr8:38436349-38569287), and was amplified at high amplitude (≥4 copies) in 15 of 155 squamous-cell lung cancer specimens (9.7%) (FIG. 1A). Of note, 11 of the FGFR1-amplified tumors were from smokers and none of these were from never-smokers (Table 1). Ten of the 15 FGFR1-amplified tumors also harbored a mutation in TP53 (Table 1).

TABLE 1

Clinical features and co-occurring mutations of FGFR1-amplified SQLC samples

| sample | overall survival | smoking history | age | gender | UICC | TP53 mutation |
|---|---|---|---|---|---|---|
| 1  | 34.4 | former  | 72 | m | Ib   | 1 |
| 2  | 9.5  | current | 76 | m | Ib   | 1 |
| 3  | 12.2 | current | 76 | m | IIb  | 0 |
| 4  | 59.6 | former  | 76 | m | IIb  | 0 |
| 5  | 22.8 | NA*     | 62 | m | IIIb | 1 |
| 6  | 31.9 | former  | 68 | m | IIb  | 1 |
| 7  | 9.4  | NA*     | 72 | m | IIIb | 1 |
| 8  | 11.8 | current | 75 | f | Ia   | 1 |
| 9  | NA*  | NA*     | 58 | m | IIIa | 1 |
| 10 | NA*  | NA*     | 76 | m | Ib   | 1 |
| 11 | 53   | current | 60 | m | Ib   | 0 |
| 12 | 152  | current | 64 | m | IIb  | 1 |
| 13 | 90   | current | 70 | m | Ib   | 1 |
| 14 | 34.5 | current | 56 | m | Ib   | 0 |
| 15 | 56.1 | current | 76 | f | Ia   | 0 |

*NA = information not available

Patients with FGFR1-amplified tumors (copy number>9 in FISH analysis) had a non-significant trend toward inferior survival compared to patients whose tumors lacked FGFR1 amplifications (copy number=2 in FISH analysis). We next analyzed copy-number alterations in lung adenocarcinoma specimens (n=77) and found no significant (q>0.25) amplification 4 copies; 1.3%) at 8p12 (FIG. 1B). Finally, we analyzed a publicly available lung cancer SNP-array dataset (Beroukhim et al., Nature 463, 899-905 (2009)) for the presence of FGFR1 amplifications (≥4 copies) and found it to occur in 6 out of 581 (1%) non-squamous cell lung cancers (FIG. 1C). Thus, FGFR1 amplification is significantly enriched in squamous-cell lung cancer when compared to our own adenocarcinoma dataset (p=0.03) and when compared to a published dataset of non-squamous-cell lung cancer (p<0.0001). Fluorescence in-situ hybridization (FISH) using an 8p12-specific probe on an independent set of 153 squamous-cell lung cancers confirmed the presence of frequent high-level amplification of FGFR1 in 34 of 153 patients (22%) (FIG. 1D and Table 2), 27 of whom were current smokers and none of whom were non-smokers.

TABLE 2

FGFR1 amplification is detected using FISH on tumor microarrays

| plate | FGFR1-HA | FGFR1-LA | FGFR1-N | sum |
|---|---|---|---|---|
| ZTMA88 | 16 | 14 | 32 | 62 |
| ZTMA86 | 18 | 14 | 38 | 70 |
| CTMA4 | 3 | 4 | 14 | 21 |
| all | 37 | 32 | 84 | 153 |
| frequency (%) | 24.18301 | 20.915033 | 54.90196 | 100 |

FGFR1-N: FGFR1 copy number = 2
FGFR1-LA: FGFR1 copy number <9
FGFR1-HA: FGFR1 copy number >9

We note that FISH is not sensitive to the admixture of non-tumoral cells. Thus, focal amplification of FGFR1 is likely to be more frequent in squamous-cell lung cancer than estimated by SNP arrays. We also sequenced the FGFR1 gene in 94 squamous-cell lung cancers and 94 adenocarcinomas and found one mutation (FGFR1$^{P578H}$) in the adenocarcinoma cohort, indicating that FGFR1 mutations might play an only minor role and might not be driver alterations in the pathogenesis of lung cancer.

Figure 2:
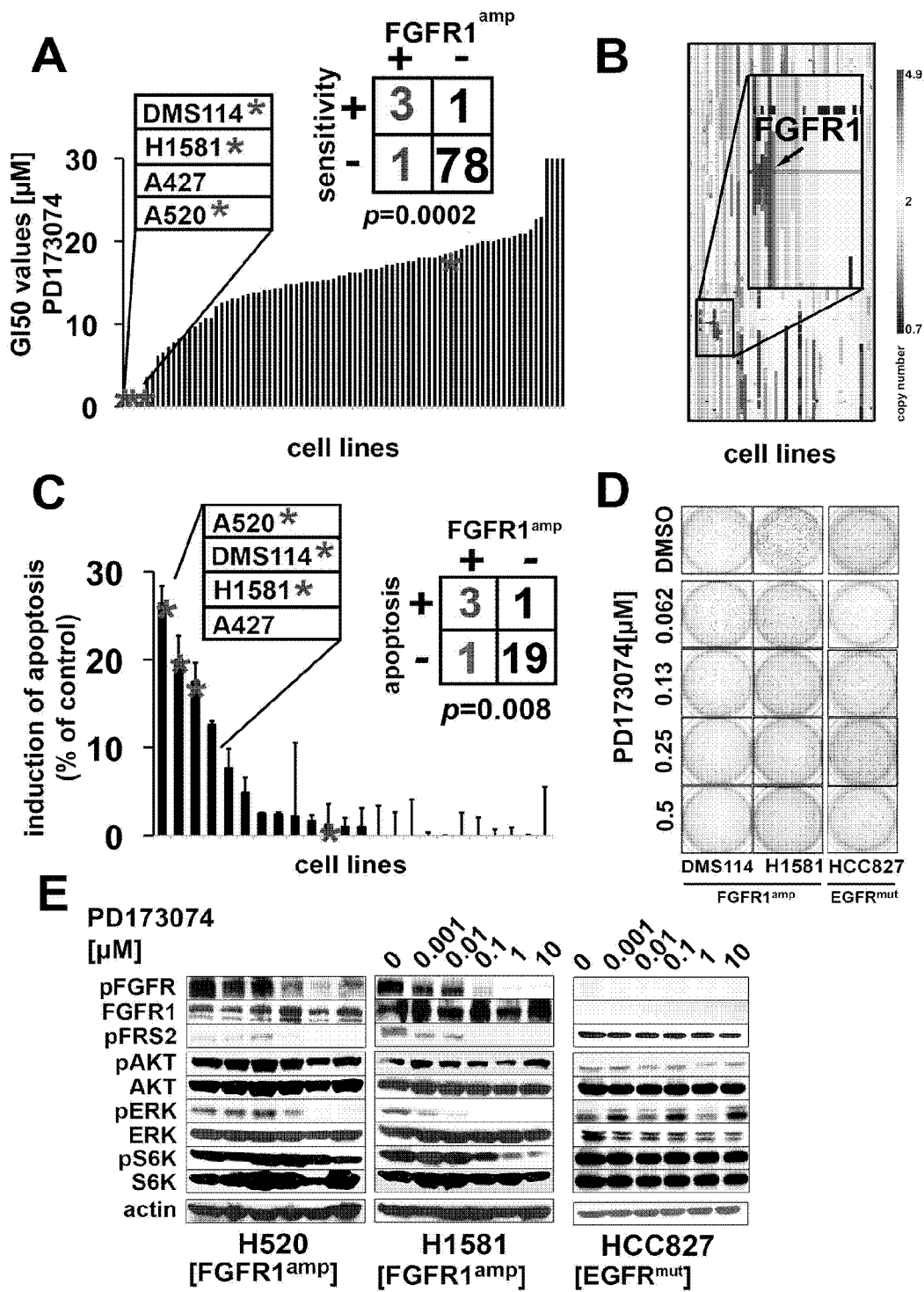
FIG. 2. FGFR1 amplification and sensitivity to FGFR inhibition. (A) $GI_{50}$-values (y-axis) of PD173074 across 83 lung cancer cell lines (x-axis). FGFR1-amplified (copy number≥4) cell lines are marked with asterisks. (B) Copy number alterations (x-axis, blue=deletion; white=copy number 2; red=amplification) on chromosome 8 with a zoom in on 8p12 (FGFR1 locus is highlighted) across all cell lines (y-axis). (C) Induction of apoptosis (difference between PD173074 at 1 μM and DMSO control after 72 h; y-axis) across 24 cell lines (x-axis; asterisks denote FGFR1 amplification copy number≥4) as measured by flow cytometry (after Annexin V/PI staining). (D) FGFR1-amplified cell lines were plated in soft agar and treated either with DMSO (control) or decreasing concentrations of PD173074. (E) Phosphorylation of FGFR and of downstream molecules in FGFR1-amplified (H1581, H520) and in FGFR1 wildtype (EGFR-mutant) cells (HCC827) after treatment with PD173074 as assessed by immunoblotting.
Figure 4:
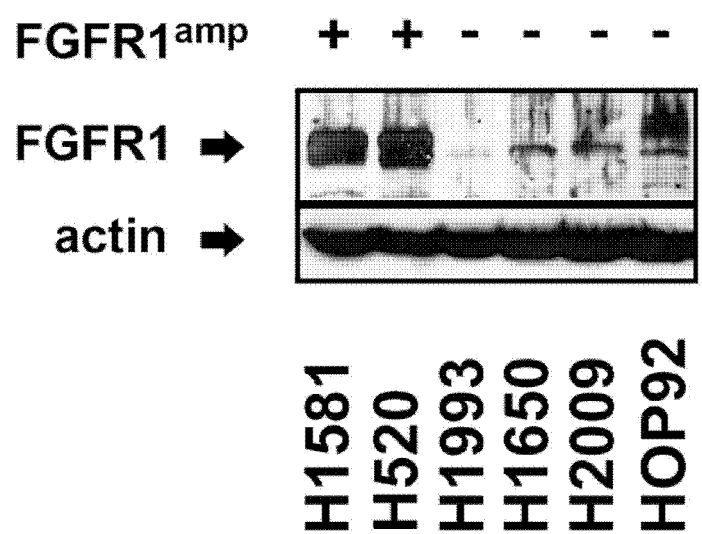
FIG. 4. FGFR1 amplification correlates with FGFR1 protein expression. Whole cell lysates from two FGFR1-amplified (indicated by "+") and four FGFR1-wildtype (indicated by "−") cells were subjected to immunoblotting and total protein of FGFR1 was detected. Actin was used as loading control.
Figure 5:
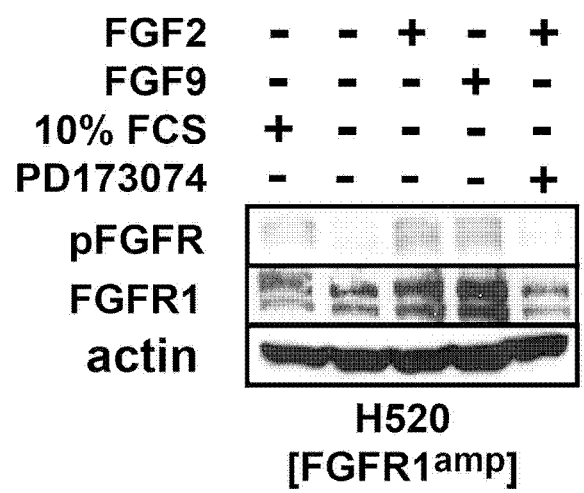
FIG. 5: The FGFR1-amplified cell line H1581 was plated in 6 cm dishes containing either FCS containing media (first lane) or serum free media and stimulated (20 minutes before harvesting) with 50 ng/ml of the indicated FGFR ligands (FGF2, lane 3 and 5; FGF9, lane 4) and treated with either 1 μM of the FGFR inhibitor PD173074 (lane 5).
Figure 6:
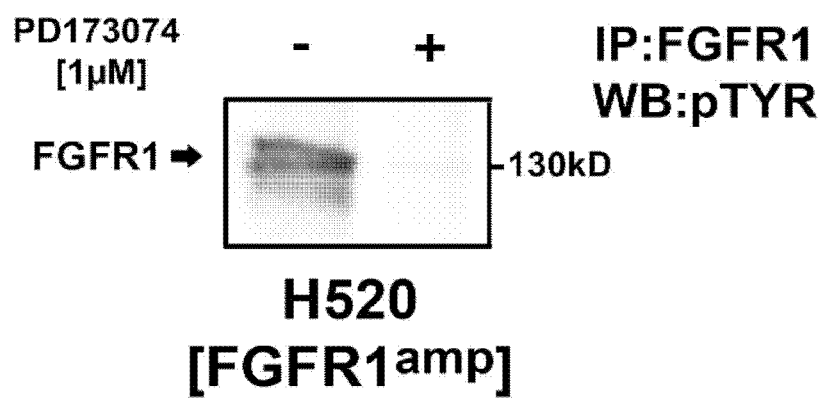
FIG. 6: Treatment of FGFR1 amplified cell line H520 with PD173074 leads to dephosphorylation of FGFR1 as measured by immunoprecipitation. Immunohistochemical detection of phosphotyrosine residues after immunoprecipitation of total FGFR1 protein of FGFR1-amplified cells (H520) before and after treatment with 1 μM PD173074 is depicted.

Next, we performed high-throughput cell-line screening (Sos et al., J Clin Invest 119, 1727-1740 (2009); McDermott et al., Proc Natl Acad Sci USA 104, 19936-19941 (2007)) to determine the activity of the non-isoform-specific FGFR inhibitor PD173074 (Mohammadi et al., EMBO J. 17, 5896-5904 (1998)) in a collection of 83 lung cancer cell lines. Of all cell lines tested, four had a half-maximal growth inhibitory concentration (GI$_{50}$ values) below 1.0 μM (FIG. 2A); Remarkably, three of the four sensitive lung cancer cell lines exhibited focal amplification at 8p12 by 6.0 SNP-array analysis (FIG. 2B) suggesting that FGFR1 amplifications are significantly (p=0.0002) associated with FGFR inhibitor activity (FIG. 2A). As expected, FGFR1-amplified cells expressed higher levels of total FGFR1 protein (FIG. 4). Interestingly, one (H520) of the three FGFR1-amplified cell lines that were sensitive to PD173074 was derived from a squamous-cell lung cancer patient. We next tested whether amplification of FGFR1 could be linked with sensitivity to FGFR inhibition in an unbiased fashion. Application of a K-nearest neighbor-based analysis, followed by leave-one-out cross validation, revealed FGFR1 amplification to be the only genetic predictor of PD173074 sensitivity that retained significance following Bonferroni-based multiple-testing correction (p<0.05). Previous reports indicated that expression of FGFR ligands might contribute to the sensitivity to FGFR inhibitors in lung cancer (Marek et al., Mol Pharmacol 75, 196-207 (2009)). We did not observe elevated levels of FGF2 in the FGFR1-amplified cell lines, nor did we observe a difference in the expression of FGFR ligands between patients harboring FGFR1 amplification and those without FGFR1 amplification. However, FGFR1-amplifed cells showed robust steady state (in serum-free media) phosphorylation that was increased upon stimulation with FGF2 or FGF9 (FIG. 5), suggesting that paracrine activation might play a role in the proliferation of FGFR1-amplified cells. We next measured induction of apoptosis in FGFR1-amplified cells after treatment with PD173074 and found a significant (p=0.008) enrichment of FGFR1-amplified lung cancer cells in the group of sensitive cells (FIG. 2C). Furthermore, FGFR inhibition led to decreased colony formation of FGFR1-amplified but not of EGFR-mutant cells in soft agar (FIG. 2D), further enforcing the notion that amplification of FGFR1 drives proliferation of these lung cancer cell lines. Treatment with PD173074 reduced the levels of phosphorylated FGFR1 (FIG. 6) and of the adaptor molecule FRS2 in a dose-dependent manner only in FGFR1-amplified cells, but not in the EGFR-mutant cell line HCC827 (Figure 2E). We also observed inhibition of phosphorylation of ERK but not of AKT and S6, indicating that the MAPK-pathway, and not the PI3K-pathway, is the major signaling pathway engaged by amplified FGFR1 (FIG. 2E).

In order to validate FGFR1 as the critical target of PD173074 in FGFR1-amplified lung cancer cells, we ectopically expressed the V561M mutation (Zhou et al., Chem Biol 17, 285-295)) at the gatekeeper position of FGFR1 (FGFR1$^{V561M}$), preventing access of the compound to the hinge region of the kinase (Blencke et al., Chem Biol 11, 691-701 (2004)). Expression of FGFR1$^{V561M}$ in FGFR1-amplified lung cancer cells abolished PD173074-mediated cytotoxicity and dephosphorylation of FGFR (FIG. 3A), consistent with the notion that FGFR1 is the critical target of PD173074 in FGFR1-amplified lung cancer cells. Furthermore, in a panel of 105 biochemically-screened kinases FGFR1 was one of only two kinases strongly inhibited by PD173074.

Figure 3:
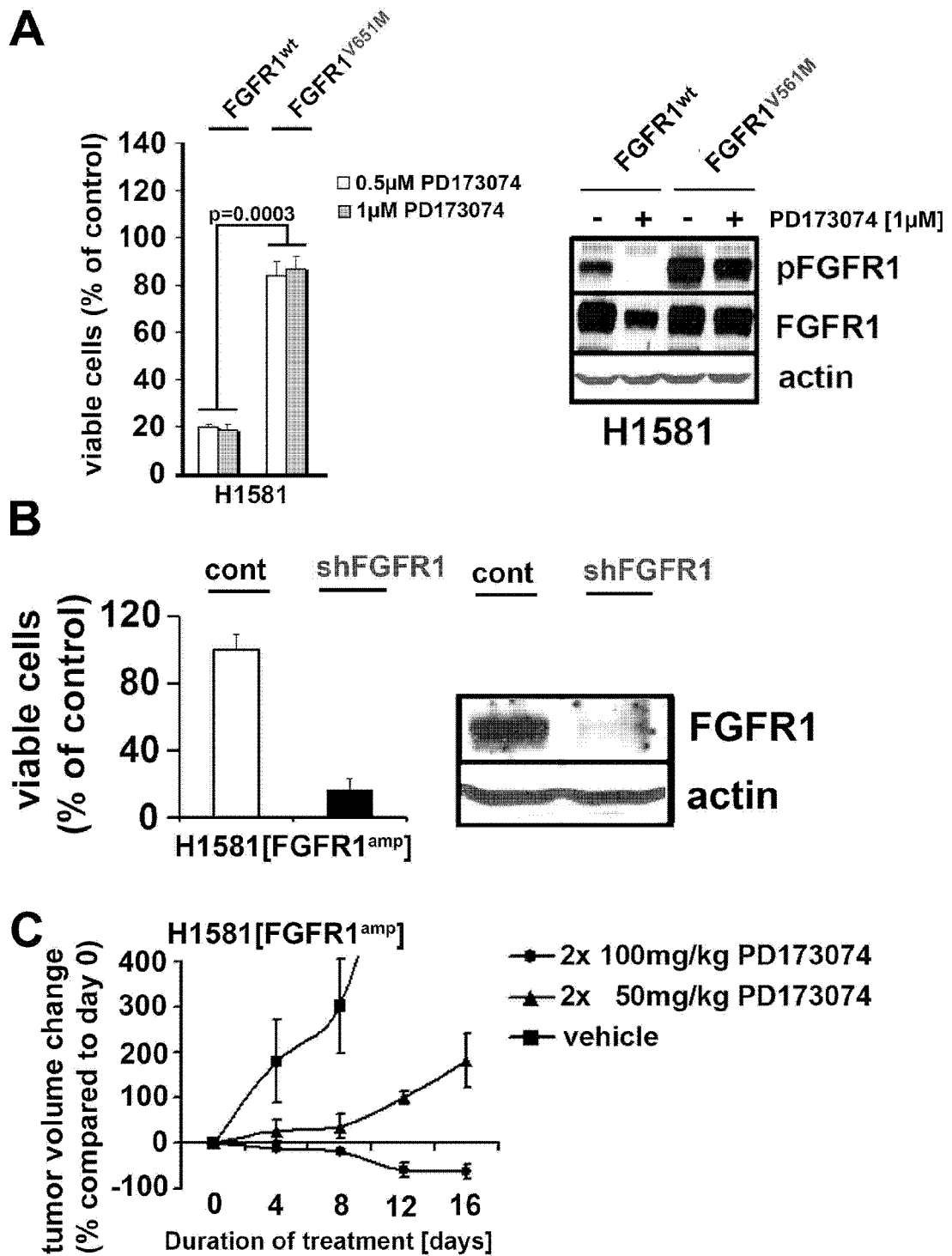
FIG. 3. FGFR1-amplified cells are dependent on FGFR1 in vitro and in vivo. (A) Left panel: Viability (PD 173074 treatment as compared to DMSO control) of FGFR1-amplified cells expressing wild-type or mutant (V561M) FGFR1 treated with PD173074 (0.5 μM white bars; 1.0 μM grey bars). Right panel: phosphorylation of FGFR in the FGFR1$^{V561M}$ and FGFR1$^{wt}$ cells detected by immunoblotting. (B) Upper panel: Viability (PD173074 treatment as compared to DMSO control; y-axis) of H1581 cells after transduction with control shRNA or shRNA targeting FGFR1. Right panel: Silencing of FGFR1 in H1581 cells was confirmed by immunoblotting (C) In mice engrafted with H1581 cells either treated with vehicle or PD173074 (dosage as indicated; y-axis), tumor volume was measured over time (x-axis).
Figure 7:
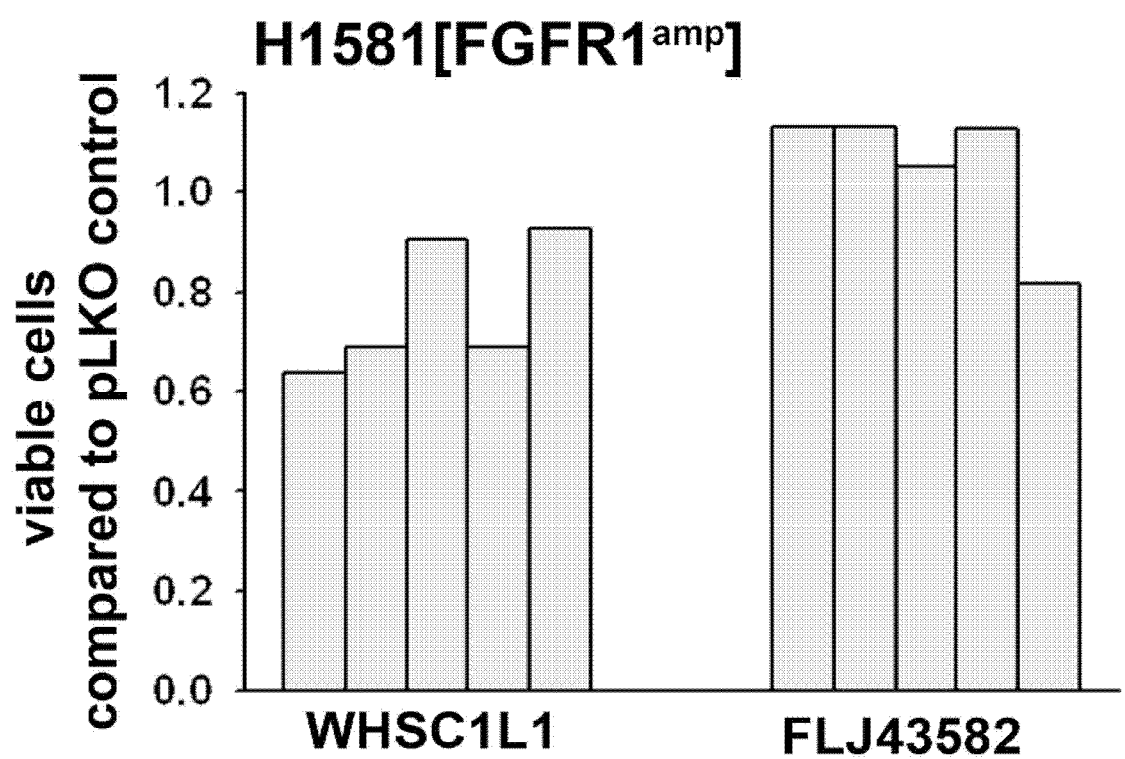
FIG. 7: Knockdown of genes adjacent to FGFR1 on 8p12 does not affect cell viability. Viability (y-axis) of FGFR1-amplified H1581 cells transduced with 5 different shRNA constructs targeting WHSC1L1 and FLJ43582 compared to cells transduced with control shRNA. Cells were selected for 7 days using puromycin (1.5 μg/ml) and counted on an automated cell counter (Z1, BeckmanCoulter).
Figure 8:
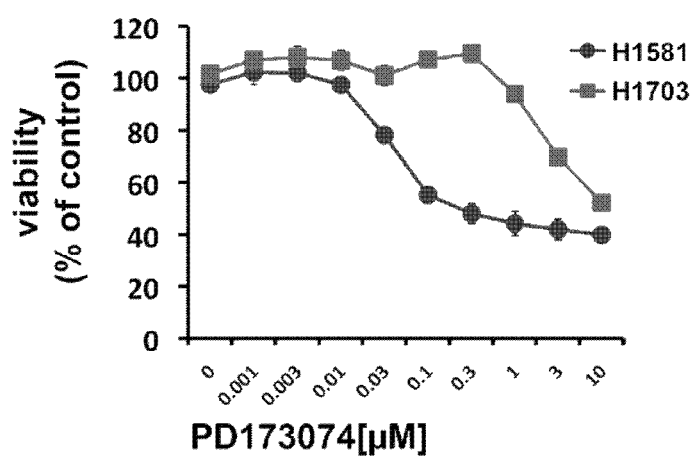
FIG. 8: PD173074 is not active in the PDGFRA- and FGFR1-amplified cell line H1703. The NSCLC cell lines H1703 (red line) and H1581 (blue line) cells were treated with increasing concentrations of PD173074 and viability was assessed measuring cellular ATP-content. Plotted are the survival curves after 96 h of compound treatment (y-axis: viability, x-axis: concentration of PD173074).

The high analytical resolution of the 6.0 SNP arrays, together with the large size of our data set, limited the number of candidate genes in the 8p12 amplicon to only two genes, FGFR1 and FLJ43582. A previous report analyzing the 8p12 locus in lung cancer applying lower-resolution techniques suggested WHSC1L1 to be the relevant oncogene in the 8p12 amplicon (Tonon et al., *Proc Nall Acad Sci USA* 102, 9625-9630 (2005)). To test whether genes other than FGFR1 drive tumorigenesis in the 8p12-amplified tumors, we silenced the genes WHSC1L1 and FLJ43582 using five different snRNA constructs in the 8p12-amplified lung cancer cell line H1581. Although silencing of either one of these genes did not inhibit cellular viability (FIG. 7), silencing of FGFR1 strongly reduced the viability of the FGFR1-amplified lung cancer cells (FIG. 3B). Of note, the cell line H1703, which bears a copy-number gain at 8p12 and that had been reported to depend on WHSC1L1 ((Tonon et al., *Proc Nall Acad Sci USA* 102, 9625-9630 (2005)) was not sensitive to FGFR inhibition (FIG. 8). By contrast, H1703 cells depend on PDGFRA for their survival (Rikova et al., *Cell* 131, 1190-1203 (2007)) due to amplification (copy number>2.8) of the gene encoding this kinase (McDermott et al., *Cancer Res* 69, 3937-3946 (2009); Ramos et al., *Cancer Biol Ther* 8, 2042-2050 (2009)). Thus, our data suggests that the gene targeted by the 8p12 amplicon is primarily FGFR1 and its amplification induces FGFR1 dependency.

Figure 9:
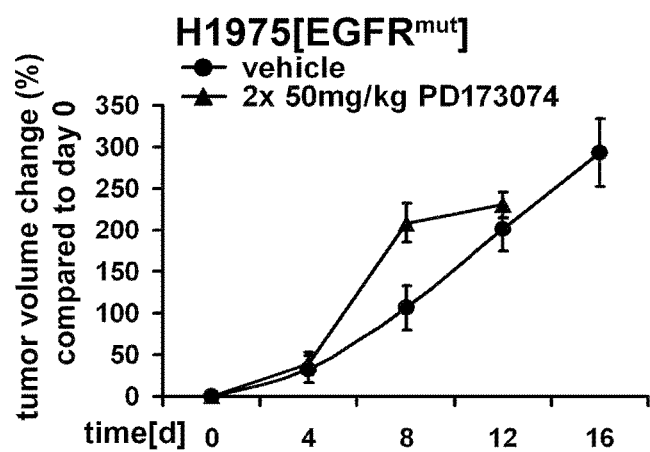
FIG. 9: Mice engrafted with H1975 (FGFR1 wild type) cells either treated with vehicle or PD173074 (dosage as indicated; y-axis). Tumor volume was measured over time (x-axis)

Finally, treatment with 100 mg/kg twice a day of PD173074 resulted in tumor shrinkage in mice engrafted with FGFR1-amplified cells (FIG. 3C). This reduction in tumor size was paralleled by reduction in the levels of phospho-ERK but not of phospho-AKT in immunohistochemical analyses of explanted tumors, validating our in-vitro findings that MAPK-signaling is the key pathway engaged by amplified FGFR1. Treatment at 50 mg/kg twice a day resulted in only a minimal exposure when compared to the gavage of 100 mg/kg twice a day due to the short half-life of the compound in vivo. By contrast, xenografted EGFR-mutant H1975 cells did not show signs of regression upon PD173074 treatment (FIG. 9). Thus, FGFR1 amplification leads to FGFR1 dependency in vivo.

Here, we have identified frequent high-level amplification of FGFR1 in squamous-cell lung cancer of smokers that sensitizes the tumors to FGFR1 inhibition. The large size of our sample set was necessary to reveal the surprisingly high prevalence of this amplicon in squamous-cell lung cancer (approximately 10%) in comparison to other lung cancer subtypes (1%). Given the insensitivity of FISH analyses to admixture of non-tumoral cells, the true prevalence of this amplification is likely to still be substantively underestimated by SNP arrays and to be up to 20%. We conclude that FGFR1 amplification is one of the hallmark alterations in squamous cell lung cancer, similar to amplification of SOX2. These two alterations were almost completely mutually exclusive, suggesting an epistatic relationship. Furthermore, FGFR1 amplification induced a strong FGFR1 dependency that could be exploited therapeutically, resulting in induction of apoptosis and tumor shrinkage in vivo. Thus, FGFR1 amplification represents an opportunity for targeted therapy in squamous-cell lung cancer. We therefore suggest that FGFR1 inhibitors, which are currently in clinical testing in tumor types bearing genetic alterations in FGFR genes (Reis-Filho et al., *Clin Cancer Res* 12, 6652-6662 (2006); Turner et al., *Nat Rev Cancer* 10, 116-129 (2009); Turner et al., *Cancer Res* 70, 2085-2094 (2010)), should be evaluated in patients with FGFR1-amplified squamous-cell lung cancer.

Materials and Methods

Genomic Analyses:

The tumor specimens analyzed in this study have been collected under local Institutional Review Board approval. All patients gave written informed consent. Genomic DNA was hybridized to Affymetrix 6.0 SNP arrays following manufacturer's instructions. Raw signal intensities were normalized and modeled using a Gaussian-mixture model. Background-corrected intensities were normalized across all arrays of one batch using quantile normalization. Raw copy numbers were calculated by dividing the normalized tumor-derived signal intensities by the mean signal intensities derived from the normal samples hybridized in the same batch. Raw copy number data were segmented using circular binary segmentation and visualized in the integrated genome viewer (IGV). GISTIC was performed as described previously. The human genome build hg18 was utilized. Dideoxy sequencing was performed on whole-genome amplified DNA of primary tumors. Cell lines were sequenced using cDNA. All primer sequences are available on request. All raw data are publically available (GEO; GSE25016).

Tissue Microarray Construction:

Tissue microarray slides were obtained from Formalin-fixed paraffin-embedded lung squamous cell carcinoma samples. The tissue microarrays contained samples of a total of 172 patients from the University Hospital Zurich, each of these samples was present in duplicate cores, each core 0.6 mm in diameter. A second tissue microarray of 22 patients from Weill Cornell Medical Center was obtained with each sample present in triplicate cores, each core 0.6 mm in diameter. Subsequently, 153 samples were used for FISH analysis.

Gene Expression:

After RNA isolation biotin labeled cRNA preparation was performed using Epicentre TargetAmp™ Kit (Epicentre Biotechnologies) and Biotin-16-UTP (10 mM; Roche Molecular Biochemicals) or Illumina TotalPrep RNA Amplification Kit (Ambion). Biotin labeled cRNA (1.5 µg) was hybridized to Sentrix® whole genome bead chips WG6 version 2, (Illumina) and scanned on the Illumina® BeadStation 500x. For data collection, we used Illumina BeadStudio 3.1.1.0 software. Gene pattern analysis platform was used to visualize the normalized data.

FGFR1 Amplification FISH Assay:

A fluorescence in-situ hybridization (FISH) assay was used to detect the FGFR1 amplification at the chromosomal level on the tissue microarrays. We performed fluorescence signal detection, with two probes on chromosome 8. The reference probe is located on a stable region of chromosome 8p23.2 and selected based on SNP array analysis. Only samples where the control BAC was detectable were used for the determination of the copy number of FGFR1. The target probe is located on the FGFR1 locus spanning 8p11.23 to 8p11.22. We used the digoxigenin labelled BAC clones CTD 2523O9 producing a green signal as reference probe. The target probe was labelled with biotin to produce a red signal using RP11-148D21 BAC clones (Invitrogen). Deparaffinized sections were pre-treated with a 100 mM Tris and 50 mM EDTA solution at 92.8 C.° for 15 min. and digested with Digest-All III (dilution 1:2) at 37° C. for 14 min.; FGFR1FISH probes were denatured at 73° C. for 5 min. and immediately placed on ice. Subsequently, the tissue sections and FGFR1FISH probes were co-denatured at 94° C. for 3 min. and hybridized overnight at 37° C. Post hybridization washing was done with 2×SSC at 75° C. for 5 min., and the fluorescence detection was carried out using streptavidin- Alexa-594 conjugates (dilution 1:200) and anti-digoxigenin-FITC (dilution 1:200). Slides were then counterstained with 4',6-Diamidin-2' phenylindoldihydrochlorid (DAPI) and mounted. The samples were analysed under a 63× oil immersion objective using a fluorescence microscope (Zeiss) equipped with appropriate filters, a charge-coupled device camera and the FISH imaging and capturing software Metafer 4 (Metasystems). The evaluation of the tests was done independently by three experienced evaluators. At least 100 nuclei per case were evaluated. The thresholds for assigning a sample to the FGFR1 "high amplification" group was copy number nine. All samples that had a copy number below nine and above two were assigned to the group of "low amplification" cohort. All the remaining samples were assigned "normal".

Cell Lines and Reagents:

Cell lines were obtained from ATCC, DSMZ, or from own and other cell culture collections and were maintained as described previously. PD173074 was purchased from commercial suppliers, dissolved in DMSO or vehicle solution and stored at $-20°$ C.

Cell-Line Screening:

Cell-line screening was performed as previously described (Sos et al., *J Clin Invest* 119, 1727-1740 (2009)) with various concentrations of PD173074. Viability was determined after 96 hours by measuring cellular ATP content (CellTiter-Glo, Promega). Half-maximal inhibitory concentrations ($GI_{50}$) were determined using the statistical data analysis software "R" with the package "ic50".

Apoptosis:

For determination of apoptosis, cells were seeded in six-well plates, incubated for 24 hours, treated with either DMSO (control) or 1.0 µM PD173074 for 72 hours and stained with annexinV and propidium iodide (PI). Finally the cells were analyzed on a FACS Canto FlowCytometer (BD Biosciences). The difference between the relative percentage of annexin V/PI positive cells treated with DMSO and cells treated with PD173074 was determined (induction of apoptosis rate).

Lentiviral RNAi and Retroviral Expression:

The V561M mutation was introduced into FGFR1 cloned in pBABE-Puro by site-directed mutagenesis. Replication-incompetent retroviruses were produced by contransfection with the pCL-ampho plasmid in HEK 293T cells. Hairpin shRNA targeting the different genes were ordered from Sigma. Replication-incompetent lentiviruses were produced from pLKO.1-Puro based vectors by contransfection with Δ8.9 and pMGD2 in 293T cells as described previously (Sos et al., *Cancer Res* 70, 868-874 (2010)). After transduction cells were selected with puromycin (1.5 µg/ml) and five days after selection cells were counted using trypan blue.

Western Blotting:

The following antibodies were used for immunoblotting: β-actin (MPBioscience), phospho-FGFR(Y653, Y654), pFRS2 (Tyr196), p-AKT (S473), pS6, S6, AKT, p-ERK, ERK (Cell Signaling Technology), total-FGFR1 (Santa Cruz), anti-rabbit-HRP, anti-mouse-HRP-antibody (Millipore).

Soft-Agar Assay:

Cells were suspended in growth media containing 10% FCS and 0.6% agar and plated in triplicate on 50 µl solidified growth medium (10% FCS; 1.0% agar). Growth medium containing indicated compound concentrations was added on top. Colonies were analyzed using the Scanalyzer imaging system (Lemnatec, Germany).

Xenograft Mouse Models:

All animal procedures were approved by the local animal protection committee and the local authorities. $5*10^6$ tumor cells were injected subcutaneously into male nude mice. After the tumors reached a size of at least 50 $mm^3$, the animals were treated twice daily by oral gavage with PD173074 (15 mg/ml for 50 mg/kg or 30 mg/ml for 100 mg/kg schedule) solved in vehicle (sodium lactate) or vehicle detergent alone. Tumor size was monitored measuring perpendicular diameters as described previously (Sos et al., *J Clin Invest* 119, 1727-1740 (2009)). For the determination of tumor growth under treatment with PD173074, each experiment presented in the figures compromises the measurement of 5 different tumors.

Statistical Analyses:

Tests for statistical significance were either two-tailed t-tests or Fishers's exact tests. Prediction of compound activity was performed using the KNN algorithm as described previously (Sos et al., *J Clin Invest* 119, 1727-1740 (2009)). Multiple hypothesis testing was performed employing the statistical data analysis software "R" using p-value adjustment.

Immunohistochemical Staining:

Mice bearing FGFR1-amplified tumors were sacrificed at the end of treatment. Tumors were exgrafted and embedded in paraffin. H&E and immunohistochemistry stainings were performed according to standard protocols (Sos et al., *Proc Natl Acad Sci USA* 106, 18351 (2009)). Antibodies recognizing pAKT, pERK, AKT and ERK were obtained from Cell signaling.

Structural Model of Compound Binding:

Amino acid side chains of gatekeeper mutant alleles of FGFR1 were modelled mith MOE (package version 2009.10, Molecular Operating Environment) based on the crystal of FGFR1 in complex with PD173074 (pdb code 2FGI) (Mohammadi et al., *EMBO J.* 17, 5896 (Oct. 15, 1998)). Figures were prepared with PyMol software (DeLano Scientific LLC).

Pharmacokinetics of PD173074:

Pharmacokinetic data were created by taking blood-samples from male nude mice by puncture of the tail-vein under isoflurane anesthesia. Blood samples of 50 µl each were drawn and mixed with 5 µl heparin (5000I.U./ml), 0.5, 1, 1.5, 2, 3, 4, 5, 6, 12, 14, 16, 18, 20, 22 and 24 hours after a single dose of either 100 or 50 mg/kg PD173074. All blood samples were centrifuged; the blood plasma-containing supernatant was extracted and stored at $-20°$ C. Analytic samples were prepared from the blood plasma by acetonitrile extraction with an internal standard of 1 µM griseofulvin. PD173074 concentrations were determined using HPLC (Shimadzu-A20) and tandem mass spectrometry (4000 Q-Trab LC-MS/NIS, AB SCIEX) with quantification limits of 63.34 ng/ml. Pharmacokinetic data was evaluated with WinNonlin Software (Pharsight).

Immunoprecipitation:

For the detection of FGFR1 phosphorylation, whole-cell lysates (0.5-1 mg) in NP40 lysis buffer was incubated with agarose A/G Plus preconjugated with the FGFR1 antibody. Immunoprecipitates were washed in NP40 lysis buffer, boiled in sample buffer, and subjected to SDS-PAGE followed by immunoblotting using an anti phospho-tyrosine residues antibody to detect specific phosphorylation of FGFR1.

Enzyme Linked Immunosorbent Assay (ELISA):

Cells were seeded in 6-well dishes, 24 h prior to the experiment. Cells were rinsed with PBS and incubated for 24 h with serum free cell culture media. Supernatants were harvested and a FGF2 ELISA (Raybiotech) was performed according to manufactures protocol. Absorbance was measured on a Mirthas LB940 (Berthold Technologies).

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be apparent that certain changes and modifications may be practiced within the scope of the appended claims.

What is claimed is:

1. A method of treating lung cancer in a human patient, the method comprising:
   detecting, in a lung cancer cell or tissue obtained from the patient, the presence of focal FGFR1 gene amplification; and
   administering a therapeutically effective amount of an FGFR1 inhibitor to the patient.

2. The method of claim 1, wherein said patient is diagnosed as having squamous cell lung cancer.

3. A method of treating lung cancer in a human patient, the method comprising:
   diagnosing the patient as having squamous cell lung cancer;
   detecting the presence of focal FGFR1 gene amplification in a squamous cell lung cancer cell or tissue obtained from the patient; and
   administering a therapeutically effective amount of an FGFR1 inhibitor to the patient.

4. The method of claim 3, wherein said patient is identified as a smoker or having a smoking history.

5. The method of claim 3, wherein said detecting comprises nucleic acid hybridization.

6. The method of claim 3, wherein said detecting comprises FISH or CISH testing or sequencing.

7. The method of claim 3, wherein said detecting comprises quantitative real-time PCR.

8. The method of claim 3, wherein said detecting comprises quantitative real-time PCR using genomic DNA from said squamous cell lung cancer cell or tissue.

9. The method of claim 3, further comprising determining the presence or absence of an EGFR-activating mutation in said squamous cell lung cancer cell or tissue.

10. The method of claim 3, further comprising determining the presence or absence of an activating mutation in the KRAS gene in said squamous cell lung cancer cell or tissue.

11. The method of claim 1, wherein the detecting of said focal FGFR1 gene amplification in said lung cancer cell is performed before or after said administering.

12. The method of claim 11, wherein said detecting comprises nucleic acid hybridization or sequencing.

13. The method of claim 11, wherein said detecting comprises in situ hybridization or immunohistochemistry.

* * * * *